United States Patent [19]

Rosen et al.

[11] Patent Number: 5,665,077
[45] Date of Patent: Sep. 9, 1997

[54] NITRIC OXIDE-RELEASING NITROSO COMPOSITIONS AND METHODS AND INTRAVASCULAR DEVICES FOR USING THEM TO PREVENT RESTENOSIS

[75] Inventors: Gerald M. Rosen, Lutherville; William R. Herzog, Jr.; Sovitj Pou, both of Baltimore, all of Md.

[73] Assignee: Nitrosci Pharmaceuticals LLC, Farmington, Conn.

[21] Appl. No.: 426,848

[22] Filed: Apr. 24, 1995

[51] Int. Cl.$^6$ ...................................................... A61M 5/32
[52] U.S. Cl. ......................... 604/266; 514/611; 128/898
[58] Field of Search ............................... 604/264–266, 604/19–21; 514/579, 611; 128/898

[56] References Cited

U.S. PATENT DOCUMENTS

| | | | |
|---|---|---|---|
| 5,212,204 | 5/1993 | Keefer et al. | 514/647 |
| 5,278,192 | 1/1994 | Fung et al. | 514/645 |
| 5,282,785 | 2/1994 | Shapland et al. | 604/21 |
| 5,286,254 | 2/1994 | Shapland et al. | 504/21 |
| 5,366,997 | 11/1994 | Keefer et al. | 514/611 |
| 5,370,614 | 12/1994 | Amundson et al. | 604/96 |
| 5,380,758 | 1/1995 | Stamler et al. | 514/562 |
| 5,405,919 | 4/1995 | Keefer et al. | 525/377 |
| 5,428,070 | 6/1995 | Cooke et al. | 514/557 |
| 5,470,307 | 11/1995 | Lindall | 604/20 |
| 5,485,827 | 1/1996 | Zapol et al. | 128/200.14 |

OTHER PUBLICATIONS

Furchgott et al., "The obligatory role of endothelial cells in the . . . ", *Nature*, vol. 288:373–376, 27 Nov. 1980.
Bailey, "Coating of Endovascular Stents", *Textbook of Interventional Cardiology*, Second Ed., vol. 2:754–765, 1994.
R. M. J. Palmer et al., "Nitric oxide release accounts for the . . . ", *Nature*, vol. 327:524–526, 11 Jun. 1987.
Snyder et al., "Biological Roles of Nitric Oxide", *Scientific American*, pp. 68–77, May 1992.
Moncada, M. D., F. R. S., et al., "Mechanisms of Disease", Epstein ed., T. *New England J. of Med.*, pp. 2002–2012, 30 Dec. 1993.
Feelisch et al., "On the Mechanism of NO Release from Sydnonimines", *J. Cardiovasc. Pharmacol.*, vol. 14, (Suppl. 11):S13–S5, 1989.
Ignarro et al., "Mechanism of Vascular Smooth Muscle Relaxation by . . . ", *T. J. of Pharmac. and Exper. Ther.*, vol. 218(3): 739–743, 22 Jun. 1988.
Kowaluk et al., "Spontaneous Liberation of Nitric Oxide Cannot . . . ", *T. J. of Pharmac. and Exper. Therap.*, vol. 225:1256–1264, 1990.

(List continued on next page.)

*Primary Examiner*—John D. Yasko
*Assistant Examiner*—Chalin Smith
*Attorney, Agent, or Firm*—Millen, White, Zelano, & Branigan, P.C.

[57] ABSTRACT

A surface of a foreign body exposed to the flowing blood of a living being which normally would promote the aggregation of platelets in that blood to form a coating firmly affixed to that surface and thus restrict the flow of blood past that surface or to form a blood clot detachable from that surface which when detached could trigger a stroke, heart attack or partial loss of lung function, such as plastic tubing, a balloon or the end of a catheter surgically inserted in a blood vessel or a stem implanted therein, e.g., in conjunction with percutaneous transluminal coronary angioplasty or the interior wall of a length of plastic tubing used to transport the blood of a patient, undergoing hypothermic surgery, inhibits such aggregation when that surface is coated with a physiologically acceptable polymer, such as polyvinyl alcohol or fibrinin, containing dissolved or dispersed therein a nitroso compound, such as 2-methyl-2-nitrosopropane, which decomposes at body temperature and in so doing releases a platelet aggregation-inhibiting amount of nitric oxide during the post-surgical period when the individual is a high risk candidate for post-surgical foreign body-mediated platelet aggregation on or at the situs of the foreign body.

22 Claims, 1 Drawing Sheet

OTHER PUBLICATIONS

Maragos et al., "Complexes of 'NO with Nucleophiles as Agents for . . . ", *J. Med. Chem.*, vol. 34(11):3242–3247, 1991.

Bates et al., "Nitric Oxide Generation from Nitroprusside by . . . ", *Biochem. Pharmac.*, vol. 42(Supp):S157–S165, 1991.

Makings et al., "Caged Nitric Oxide", *T. J. of Biol. Chem.*, vol. 269(9): 6282–6285, 4 Mar. 1994.

Wajer et al., "C–Nitroso Compounds–II on the Photochemical and . . . ", *Tetrahedron*, vol. 23:4021–4026, 1967.

Byron et al., "Effects of Heat Treatment on the Permeability of . . . ", *J. of Pharmac. Sciences*, vol. 76(1):65–67, 1987.

Maassen et al., "Silver Carbonate, a Convenient Reagent for Preparing . . . ", *RECUEIL*, vol. 90:373–376, 1971.

Pou et al., "Biological Studies of a Nitroso Compound that Releases . . . ", *Mol. Pharmac.*, vol. 46:709–715, 1994.

The Merck Index, 10th edition, pp. 583–584.

NITRIC OXIDE-RELEASING NITROSO COMPOSITIONS AND METHODS AND INTRAVASCULAR DEVICES FOR USING THEM TO PREVENT RESTENOSIS

BACKGROUND OF THE INVENTION

1. Field of the Invention

This invention relates generally to novel nitric oxide-releasing nitroso compositions and drug delivery systems and method for using them, more particularly for the prevention of restenosis after percutaneous transluminal coronary angioplasty, and for the prevention of acute or subacute thrombic occlusion related to the use of or deployment of a synthetic device within the vascular tree.

2. Description of the Prior Art

In 1980, Furchgott and Zawadzki (*Nature*, 288: 373–376, 1980) found that acetylcholine induced vascular relaxation in pre-contracted aortic rings, which was dependent upon the presence of the endothelium. Based on a series of elegant experiments, these scientists proposed that the endothelial cells, stimulated by the presence of acetylcholine, released a factor, which diffused to the underlying smooth muscle, resulting in relaxation of the tissue. They termed this factor, Endothelial-Derived Relaxation Factor (EDRF). In 1987, Palmer and co-workers (*Nature*, 327:524–526, 1987) determined that the free-radical, nitric oxide, exhibited many of the physiologic properties reported for EDRF. Besides regulating vascular tone, nitric oxide has been found to: (a) inhibit neutrophil adhesion, (b) antagonize platelet aggregation and (c) enhance macrophage-mediated microbial killing (See, S. H. Snyder and D. S. Bredt, *Sci. Amer.* 68–77, May 1992; S. Moncada and A. Higgs, *New Engl. J. Med.* 329:2002–2012, 1993).

Since nitric oxide appears to be central to the regulation of many physiologic functions, it is not surprising that this free radical can attenuate many pathological conditions, which, in the absence of nitric oxide, would result in severe injury. However, because nitric oxide is a gas, it is not suitable for administration systemically to treat a localized abnormality or disease because a nontoxic therapeutically effective dosage, in those circumstances, is difficult, if not impossible, to achieve. Even if it were possible to carefully titrate the dose of nitric oxide to minimize systemic toxicity, it would be very difficult to deliver locally an effective dose to a site of inter- est. Therefore, the development of therapeutic agent, which would mimic the pharmacological action of nitric oxide, has received considerable attention. Several classes of nitric oxide-releasing compounds have been developed, including syndnoeimine (Noack and Feelisch, *J. Cardiovasc. Pharmacol.*, 14S:51–55, 1989), nitroglycerin (Noack and Feelisch, *J. Cardiovasc. Pharmacol.*, 14S:51–55, 1989), S-nitrosoderivatives (Ignarro, Lippton, Edwards, Baribos, Hyman, Kadowitz and Gretter, *J. Pharmacol. Exp. Ther.*, 218:739–729, 1981; Kowaluk and Fung, *J. Pharmacol. Exp. Ther.*, 255:1256–1254, 1990), and N-nitroso compounds (Maragos, Morley, Wink, Dunams, Saavedra, Hoffman, Bove, Isaac, Hrabie and Keefer, *J. Med. Chem.*, 34:3242–3247, 1991). These compounds require activation, either through hydrolysis or oxidation to generate nitric oxide. Alternatively, several studies have photolyzed "caged-nitric oxide" compounds, generating nitric oxide. For example, the organometallic-containing compound, nitroprusside, has been reported to release nitric oxide upon light activation (Bates, Baker, Guerra and Harrison, *Biochem. Pharmacol.*, 42S:S157–S165, 1991). Contrary to this, nitric oxide generation from light activation of ruthenium nitrosyl trichloride failed to inhibit platelet aggregation, thereby questioning the utility of this approach (Makings and Tsien, *J. Biol. Chem.*, 269:6282–6285, 1994). Finally, 2-methyl-2-nitrosopropane upon photolysis can liberate nitric oxide through light-induced homolytic cleavage of the carbon-nitrogen bond (Pou, Anderson, Surichamorn, Keaton and Tod, *Mol. Pharmacol.*, 46:709–715, 1994).

Apparatuses and methods have been developed for delivering nitric oxide-releasing compounds and other drugs selectively and locally to a selected internal body tissue site, e.g., for preventing restenosis after percutaneous translumina/coronary angioplasty. An example is U.S. Pat. No. 5,282,785, which employs a drug delivery apparatus, comprising a flexible catheter for insertion into an internal target area of the body and a drug delivery means connected to the catheter. In this version, the latter delivers the drug in a radically restricted manner and comprises (a) a drug delivery chamber at the distal end of the drug delivery apparatus, which has a selectively permeable outer membrane portion and circumferential lips adjacent both the proximal and distal ends of the drug delivery system to minimize movement of a drug beyond a segment of internal tissue and a fluid delivery passageway extending from the chamber to the proximal end of the catheter; and (b) a non-permeable balloon affixed to and surrounding a portion of the chamber, which, when inflated, secures the chamber at the target area and radially restricts local delivery of the drug by providing intimate contact between the balloon and a portion of the internal body tissue. The apparatus also includes means of assisting the transport of the drug across the selectively permeable outer membrane with or without application of pressure.

Similarly, U.S. Pat. No. 5,286,254, which also employs an apparatus, comprising a flexible catheter having a distal end and a proximal end and which is adapted for insertion into an internal area of a body; a drug delivery means having a fluid delivery passageway for delivering a drug to the distal end of the apparatus, an outer wall and a selectively permeable microporous outer membrane portion proximate to the distal end and an impermeable end to enhance delivery of the drug to the target area; and phoresis means for assisting the transport of the drug across the selectively permeable membrane.

These similar types of apparatuses have the disadvantage, as do most intravascular devices, of promoting platelet deposition at the site where the device is located, as is the case of stents or after removal of a device at a vascular site, which has received treatment with either a balloon angioplasty or the delivery device as described in U.S. Pat. No. 5,282,785 and U.S. Pat. No. 5,286,254.

The method of this invention provides a method of decreasing platelet aggregation, either in the form Of a coating that builds up on a medical device that is permanently implanted in a blood vessel or that comes in contact with the circulating blood of a living being on a temporary basis or in the form of a detachable dot which, if it travels to the brain, lung or heart, can be a debilitating or life threatening sequelae to a cardiovascular surgical procedure.

SUMMARY OF THE INVENTION

In a method aspect, this invention relates to a method for the prevention of the aggregation of platelets from blood flowing in a living being resulting from exposure of the blood to a foreign body, which comprises coating the surface of the foreign body which contacts the blood prior to contact therewith, with a physiological acceptable polymer which is insoluble in the blood and which contains dissolved or dispersed therein an amount of a nitroso compound which slowly decomposes at body temperature and in so doing relases an amount of nitric oxide from the coating effective to inhibit the platelet aggregation which would otherwise be promoted by the foreign body.

In a composition of matter aspect, this invention relates to an aqueous liquid coating composition comprising (a) an aqueous vehicle; (b) an injectable physiologically acceptable polymer dissolved or dispersed in the vehicle; and (c) a nitroso compound which slowly decomposes at body temperature and in so doing produces nitric oxide, wherein the polymer is precipitable from the aqueous vehicle, e.g., by altering the pH or ionic strength of the aqueous vehicle, and the concentration of the nitroso compound in the aqueous vehicle is effective to generate a platelet aggregation-inhibiting amount of nitric oxide when the polymer with the nitroso compound occluded therein is deposited on a platelet aggregation promoting surface within the body of a living being.

In an article of manufacture aspect, this invention relates to an intravascular medical device, such as a balloon or catheter tip adapted for insert in or a stent adapted for implantation onto the inner wall of a blood vessel, e.g., in conjunction with percutaneous transluminal angioplasty, whose surfaces which are in contact with the blood stream of a living being are coated with a coating of a physiological acceptable polymer which is insoluble in blood and which contains dissolved or dispersed therein an amount of a nitroso compound which slowly decomposes at body temperature over a prolonged period and in so doing releases nitric oxide at a rate effective to prevent the platelet aggregation which could otherwise occur when the stent is implanted in a blood vessel.

BRIEF DESCRIPTION OF THE DRAWINGS

The drawing depicts an otherwise conventional surgical stent 1, adapted for implantation into the section of a blood vessel which has been subjected to coronary angioplasty, in the form of a length of an open weave tube formed from a plurality of interwoven stainless steel wires 2, for attachment to the interior wall of the blood vessel, which wires have a membranous transparent coating 3 thereon and the interstices therebetween have a film of fibrin which contains a nitric oxide-releasing nitroso compound.

DETAILED DESCRIPTION

Figure 1:
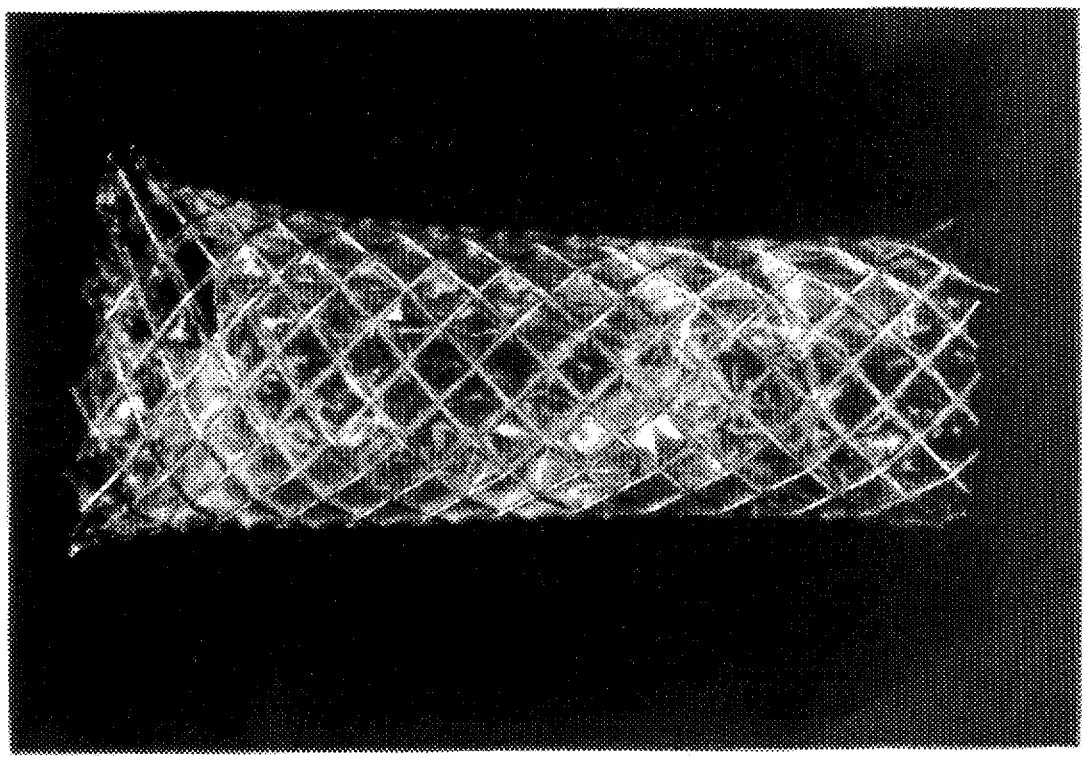

This invention is based on the discovery that the aggregation of platelets in blood as a result of exposure of the blood to a foreign body or to the injured endothelium can be inhibited by coating at least the surface of the foreign body to which the circulating blood is exposed with a coating containing an amount of nitroso compound which is stable at room temperature but at body temperature is unstable and releases from the coating a platelet aggregating-inhibiting amount of nitric oxide, which amount achieves a nitric oxide concentration locally at the surface of the foreign body which cannot safely be achieved by the administration of a nitric oxide-releasing compound systemically, whether per se or by intramuscular injection or by injection directly into the blood vessel itself.

Examples of such nitroso compounds are a-substituted nitroso compounds, such as 2-methyl-2-nitrosopropane. See Wajer, A. J. W. et al., *Tetrahedron*, 23: 4021–4026, 1967.

These compounds are in equilibrium between a stable dimer form of the formula

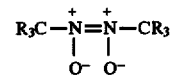

and a nitric oxide-releasing monomer form of the formula $R_3C-N=O$ wherein each R is an inert monovalent group, e.g., hydrocarbon, preferably alkyl, more preferably straight or branched lower ($C_{1-4}$) alkyl, which can be alike or different and which can be unsubstituted or substituted, e.g., 2-methyl-2-nitrosopropane or a corresponding group substituted by a non-reactive (chemically and physiologically while in situ), moiety, such as, for example, $-C(CH_3)_2CH_2OH$, $-C(CH_3)_2CH_2OR_1$, $-C(CH_3)_2CH_2OAc$, $-C(CH_3)_2Aryl$, $-C(CH_3)(Aryl)_2$ or $-C(Aryl)_3$ in which $R_1$ is an alcohol moiety, e.g., of a hydrocarbon alcohol, such as an alkanol, preferably of 1–4 carbon atoms, e.g., methyl or ethyl; Ac is the acid moiety of an organic acid, e.g., a fatty, preferably lower-alkanoic, acid, e.g., acetate, and Aryl is phenyl or other unsubstituted or substituted monocyclic or polycyclic carbocyclic or heterocyclic moiety, which at room temperature (18°–24° C.) or below exist in a stable equilibrium between monomer and dimer. At this temperature, the dimer form predominates. However, as the temperature approaches 37° C., the equilibrium shifts to the monomer, resulting in the release of nitric oxide. The concentration of nitric oxide achieved at the surface of the foreign body is dependent upon the concentration of nitroso-containing compound.

This invention relates to methods, compositions and articles of manufacture useful in the prevention of platelet deposition either on a foreign body introduced surgically into a blood vessel or at vascular sites which have received treatment, e.g., balloon angioplasty or stem implantation. The reduction of platelet deposition has important implications for reducing the likelihood of the phenomenon of restenosis occurring following balloon angioplasty. By impregnating the polymer used to coat an implantable intravascular device such as a metal stent (as shown in the drawing) with a nitroso-containing compound, nitric oxide can be locally delivered at a low dose which can be controlled by varying the concentration of the nitroso-containing compound and the nature of the polymer forming the coating on the implantable intravascular device. With such an approach, systemic nitric oxide toxicity, e.g., hypotension, can be prevented from occurring.

The nitroso compounds employed in the composition of this invention are:

(a) non-toxic, that is, substantially free from any significant toxic effects at their effective applied concentration;

(b) substantially free of symptomology, that is, they do not produce significant symptoms detectable to the person treated at their effective applied concentration;

(c) relatively stable at room temperature, i.e., once a nitroso containing compound is impregnated into a polymer and coated onto a stent or other device, nitric oxide is not released therefrom at a significant rate, e.g., during the preparation of the coating or its application to the stent or other device or thereafter, during shelf storage in a packaged container at a rate greater than 1% per month;

(d) long lasting, that is, once a stent or other intravascular device bearing on the surface thereof the polymer impregnated with the nitroso compound is inserted into a blood vessel, the duration of the delivery of nitric oxide can be adjusted by varying the concentration of the nitroso compound in the polymer to conform to the clinical situation to be a matter of minutes, e.g., 5–90 minutes, in the case of a angioplasty balloon or catheter, hours, e.g., 1–4 hours in the case of hypothermic surgery blood circulating pump plastic tubing, or days or weeks, e.g., 1–14 days or longer, in the case of a stent.

The nitroso compound employed in this invention, i.e., a compound of the formula $R_3C-N=O$ wherein R is a tertiary carbon atom-linked radical as defined hereinabove, is produced and releases nitric oxide through homolytic cleavage of the carbon-nitrogen nitroso bond to yield the nitric oxide free radical ($\bullet N=O$) in accordance with the following reaction scheme:

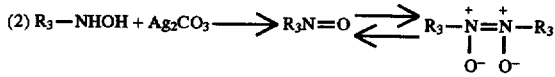

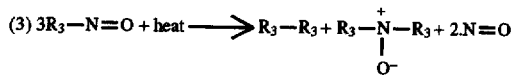

wherein R is as defined above.

The nitric oxide-releasing reaction is temperature dependent, i.e., it increases at elevated temperatures. Therefore, the selected nitroso compound should be one in which the reaction occurs at the desired rate at the body temperature of a being treated in accordance with this invention. The nitroso compounds employed in this invention, e.g., 2-methyl-2-nitrosopropane, are soluble in water, thus allowing the preparation thereof over a wide concentration range. For example, a 1 mM solution of 2-methyl-2-nitrosopropane in HEPES buffer at pH 7.4 and at 37° C. releases only 20% of the available nitric oxide in one hour.

The coating on the foreign body preferably is from 0.1–1.0 mm thick and contains from 1 μmoles to 100 μmoles of nitroso compound per $mm^2$. Higher concentrations are desirable when the diffusion rate of the nitric oxide from the polymer is very slow or when it is desired that the release of the nitric oxide occurs over a prolonged period of time, e.g., more than 48 hours.

A wide variety of suitable tert.-C-nitroso compounds of can be synthesized by reducing a nitroalkane with $Zn/NH_4Cl$ to the corresponding N-hydroxylamine according to the method of Bonnett et al., *J. Chem. Soc.*, 2094–2102, 1959, followed by oxidation using silver carbonate ($Ag_2CO_3$). See Maasen and DeBoer, *Rec. Trav. Chim.*, 90:373–376 1971.

A wide variety of polymers can be used to encapsulate the nitric oxide-releasing nitroso compound, including both physiologically inert and biodegradable polymers and those which are only slowly soluble and those which are insoluble in blood. The insoluble polymers which are suitable are those which form a permeable membrane coating around the foreign body so that the nitric oxide can migrate therefrom as it is produced. When the foreign body is inserted into the living being, it preferably is physiologically inert and, when permanently implanted, also biogradable. Examples of biodegradable polymers which can be used as drug delivery systems including the natural polymers: (1) collagen, (2) albumin, (3) casein, (4) fibrin and (5) gelatin [S. Bogdansky, in: *Biodegradable Polymers as Drug Delivery Systems*, Ed. by M. Chasin and R. Langer, Marcel Dekker, Inc., New York, pp. 231–259, 1990]. Synthetic polymer systems include: polylactide and polyglycolide [D. H. Lewis, in: *Biodegradable Polymers as Drug Delivery Systems*, Ed. by M. Chasin and R. Langer, Marcel Dekker, Inc., New York, pp. 1–42, 1990]; polyvinyl alcohols [P. R. Byron and R. N. Dalby, *J. Pharm. Sci.*, 76:65–67, 1987]. Human or porcine fibrin is especially preferred. Examples of synthetic polymers are the polyvinyl alcohols and polyalkylene oxides.

The characteristics of an "ideal" coating for a stent is one which: can be applied to luminal or subluminal surface; does not cause a significant increase in stent wall thickness; is stable over time without desquamation; has a surface tension below 30 dyne/cm; has a smooth surface texture (<1 μm irregularities); has a negative or neutral surface charge; allows rapid endothelialization; permits timed elution of the nitric oxide; and delivers an effective concentration locally of the nitric oxide. See S. R. Bailey, "Coating of Endovascular Stents" in *Textbook of Interventional Cardiology*, ed. by E. J. Topol, Vol. 2, 2nd edition, W. B. Saunders, Philadelphia, pp. 754–765 (1994).

The desired coating can be formed by immersing the foreign body in a solution or colloidal dispersion of the selected polymer in an aqueous vehicle containing the nitroso compound and then insolubilizing the polymer, e.g., by changing the pH or the ionic strength of the vehicle or denaturing a proteinaceous polymer, so that a coating of the polymer containing the nitric oxide-releasing nitroso compound occluded therein deposits on the exposed surfaces of the foreign body. For example, a stent is placed in platelet-rich plasma which contains the nitric oxide releasing compound. The surface of the stent is thereby coated with a solution of platelet-rich human or porcine plasma containing the nitric oxide releasing compound and fibrin which is precipitated onto the surface of the stent. The rate at which nitric oxide will be secreted from the coating on the stent when the stent is surgically implanted in a blood vessel can be determined by placing the coated stent in a buffer solution, pH 7.4 at 37° C., and measuring $\bullet NO$ concentration in the buffer solution at periodic intervals.

The foreign body can be any medical device or product which has a surface which is exposed to the blood stream of a living being and is susceptible to neutrophil adhesion thereto or which promotes platelet aggregation. Intravascular devices and angioplasty surgery in general frequently promotes restenosis. Therefore, patients who have undergone a percutaneous transluminal coronary angioplasty, with or without a stent implant, require extended hospitalization after surgery because of their susceptibility to restenosis. Similarly, patients undergoing blood flow diversion outside the body, e.g., in conjunction with hypothermic surgery, have increased susceptibility to platelet aggregation due to a foreign body response resulting from the exposure of the blood to the plastic tubing used to transport the blood. A similar risk of foreign body response occurs in patients undergoing anglograms as a result of the insertion of plastic tubing into an artery. Therefore, anticoagulants are conventionally administered (with their unavoidable associated risks) to suppress this response when the interior of the tubing is coated with coating according to this invention, anticoagulants can be reduced or even eliminated entirely. Synthetic or reconstituted natural, e.g., from powdered bone and binder, bony structures can also trigger a foreign body response and therefore can benefit from a coating thereon according to this invention. A preferred embodiment of the intravascular device aspect of this invention is a metal, e.g., stainless steel or polymeric, intravaseular stent which typically is implanted temporarily or permanently in a blood vessel after percutaneous transluminal coronary angioplasty.

From the foregoing description, one skilled in the art can easily ascertain the essential characteristics of this invention, and without departing from the spirit and scope thereof, can make various changes and modifications of the invention to adapt it to various usages and conditions. The entire disclosures of all applications, patents and publications, cited above and below, are incorporated by reference. The following preferred specific embodiments are, therefore, to be construed as merely illustrative and not limitative of the disclosure in anyway whatsoever. In the foregoing and in the following examples, all temperatures are set forth uncorrected in degrees Celsius and unless otherwise indicated, all parts and percentages are by weight.

EXAMPLES

Example I

To prepare a polymer coated stent, platelet-rich human or porcine plasma (PRP) is obtained via centrifugation, at 1,000 rpm for 15 minutes, of citrated whole blood. In a test tube containing 5 mL of the platelet-rich plasma is added 2-methyl-2-nitrosopropane (Aldrich Chemical Co.) to bring its concentration in the plasma to 100 µM followed by an excess of thrombin, thus stimulating clot formation. A stainless steel stent (9 mm diameter; 28 mm length, formed of interwoven 0.17 mm stainless steel wire) is placed in the plasma at room temperature. After organization of the clot, which takes about 35–50 min., the stent is removed and air dried, which takes about 4–5 hrs. This process leaves a translucent 2-methyl-2-nitrosopropane-containing fibrin film as a coating on the walls of the stent and an intersficial membrane enveloping the stent.

Example II

A stainless steel stent is placed in a test tube containing 5 mL of the platelet-rich plasma, prepared as described above. To this platelet-rich plasma is added 2-ethyl-2-nitrosopropane (100 µM, final concentration) in the dark just prior to the addition thereto of a cell-aggregating amount of thrombin. The test tube is covered in aluminum foil to prevent light induced cleaving of the nitroso compound. The process for coating the stent is as described above. Verification that the nitric oxide-releasing compound is present in the coated stent is based on measuring uptake of the nitroso compound into the fibrin and the detection of nitric oxide, when the fibrin coated stent is placed in phosphate buffer, pH 7.4 at 37° C., using the oxyhemoglobin method of Pou, Anderson, Surichamorn, Keaton and Tod, *Mol. Pharmacol.*, 46:709–715, 1994. By varying the concentration of nitric oxide-releasing compound in the platelet-rich plasma into which the stent is dipped, the nitric oxide (nitric oxide release rate) can be varied as desired.

Example III

To prepare a synthetic polymer coated stent, a 1% (w/v) aqueous solution, prepared by heating a dispersion of polyvinyl alcohol in water at 60° C. for 2 hours as described in Byron and Dalby [*J. Pharm. Sci.*, 76:65–67, 1987], to which 2-methyl-2-nitrosopropane is dissolved in the dark, after cooling to 10° C., to a final concentration of 100 µM. In the dark, the polyvinyl alcohol solution containing the nitric oxide-releasing agent is then poured over the stent and dried in the dark at room temperature overnight. A polyvinyl alcohol film containing 2-methyl-2-nitrosopropane is then deposited as a coating on the walls of the stent.

Example IV

A stent was carefully placed in the PRP, so that the plasma covered it completely. Thrombin (Armour Pharmaceutical Co., Collegeville, Pa.) diluted in distilled water (1000 units of thrombin in 5.0 cc of water) was then added to the PRP at a concentration of 0.3 cc of thrombin per 1 cc of plasma. This procedure resulted in the immediate formation of a clot around the stent. The clot and tube were maintained for 2 hours at room temperature for clot organization and then placed under a ventilated hoed to dry. In 24–36 hours, the system had dried completely, resulting in the stent coated with human fibrin, as shown in the drawing.

Example V

An angioplasty balloon device comprising a catheter, wires and balloon is coated with a coating of fibrin or polyvinyl alcohol containing 1–100 µmoles of 2-methyl-2-nitrosopropane as the nitric oxide-releasing compound is delivered to the appropriate arterial site using standard angioplasty techniques. After expansion of the balloon for about 10 minutes, the balloon is then deflated and the device removed. The nitric oxide device released from the device during the angioplasty procedure inhibits platelet adhesion to the site of angioplasty.

Example VI

The interior surface of tubing used to transport blood from and back to a patient undergoing hypothermic surgery is coated by filling the tubing with a platelet-rich plasma solution of 2-methyl-2-nitrosopropane and thrombin or polyvinyl alcohol as described above at room temperature or below until a fibrin coating containing the 2-methyl-2-nitrosopropane forms on the inner wall of the tubing. Tubing thus treated inhibits platelet aggregation in the blood of the patient undergoing the hypothermic surgery.

The preceding examples can be repeated with similar success by substituting the generically or specifically described reactants and/or operating conditions of this invention for those used in the preceding examples. For example, the tip of a catheter used to scrape a deposit from the interior wall of an artery can similarly be coated.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the prevention of the aggregation of platelets from blood flowing in a living being resulting from exposure of the blood to a foreign body, which comprises coating the surface of the foreign body which contacts the blood prior to contact therewith, with a physiologically acceptable polymer which is insoluble in the blood and which contains physically dissolved or dispersed therein an amount of an α-substituted nitroso compound which slowly thermally decomposes at body temperature over a prolonged period and in so doing releases an amount of nitric oxide from the coating at a rate effective to inhibit the platelet aggregation which would otherwise be promoted by the foreign body.

2. A method according to claim 1, wherein the polymer is biogradable.

3. A method according to claim 2, wherein the polymer is human fibrin which is precipitated onto the surface of the foreign body from a plasma solution thereof with thrombin.

4. A method according to claim 1, wherein the nitroso compound is in equilibrium with a stable dimer of the formula

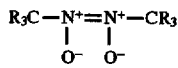

and a nitric oxide-releasing monomer of the formula $R_3C-N=O$ wherein each R is an inert monovalent group.

5. A method according to claim 1, wherein the living being is a human.

6. A method according to claim 5, wherein the foreign body is the inner surface of plastic tubing used to transport the blood of a patient undergoing hypothermic surgery.

7. A method according to claim 5, wherein the foreign body is a balloon, a catheter or a stent inserted surgically into a blood vessel of a human in conjunction with transluminal coronary angioplasty, the polymer is biogradable and the nitroso compound is 2-methyl-2-nitrosopropane.

8. A method according to claim 7, wherein the foreign body is a stent and the polymer is human fibrin which is precipitated onto the surface of the stent from platelet-rich plasma with thrombin.

9. A method according to claim 5, wherein the foreign body is an intravascular device which is inserted surgically into a blood vessel of a human in conjunction with percutaneous transluminal coronary angioplasty.

10. A method according to claim 9, wherein the foreign body is a stent.

11. A method according to claim 10, wherein the coating is applied to all of the exposed surfaces of the stent.

12. An intravascular device adapted for insertion into a blood vessel of a living being, whose exterior surface is coated with a coating of a physiologically acceptable polymer which is insoluble in blood and which contains physically dissolved or dispersed therein an amount of an α-substituted nitroso compound which slowly thermally decomposes at the body temperature of the living being over a prolonged period and in so doing releases nitric oxide the platelet aggregation which could otherwise occur when the stent is implanted in a blood vessel.

13. A stent according to claim 12, wherein the polymer is biodegradable.

14. A stent according to claim 12 wherein the nitroso compound is 2-methyl-2-nitrosopropane.

15. An intravascular device according to claim 12, wherein the nitroso compound is in equilibrium with a stable dimer of the formula

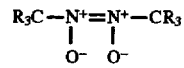

and a nitric oxide-releasing monomer of the formula $R_3C-N=O$ wherein each R is an inert monovalent group.

16. A metal stent according to claim 12.

17. A stent according to claim 16, wherein the polymer is human fibrin.

18. An aqueous liquid composition comprising (a) an aqueous vehicle; (b) an injectable physiologically acceptable polymer dispersed in the vehicle; and (c) an α-substituted nitroso compound which thermally decomposes at body temperature over a prolonged period of time and in so doing produces nitric oxide, wherein the polymer is precipitable from the aqueous vehicle with the nitroso compound physically occluded therein by altering the pH or ionic strength of the aqueous vehicle and the concentration of the nitroso compound in the aqueous vehicle is effective to generate a platelet aggregation-inhibiting amount of nitric oxide when the polymer with the nitroso compound occluded therein is deposited on a platelet aggregation promoting surface within the body of a living being.

19. A composition according to claim 18, wherein the nitroso compound is in equilibrium with a stable dimer of the formula

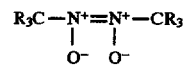

and a nitric oxide-releasing monomer of the formula $R_3C-N=O$ wherein each R is an inert monovalent group.

20. A composition according to claim 14, wherein the polymer is biogradable.

21. A composition according to claim 20, wherein the polymer is human fibrin.

22. A composition according to claim 21, wherein the nitroso compound is 2-methyl-2-nitrosopropane.

* * * * *